United States Patent [19]

Brewster

[11] Patent Number: 4,668,698

[45] Date of Patent: May 26, 1987

[54] [(4-PHENYL-1,3-DIOXAN-CIS-5-YL)ALKYL]-PHENYLALKANOIC ACID DERIVATIVES

[75] Inventor: Andrew G. Brewster, Macclesfield, United Kingdom

[73] Assignee: Imperial Chemical Industries PLC, London, England

[21] Appl. No.: 670,019

[22] Filed: Nov. 9, 1984

[30] Foreign Application Priority Data

Nov. 11, 1983 [GB] United Kingdom ............... 8330094

[51] Int. Cl.$^4$ .................. A61K 31/335; C07D 319/06
[52] U.S. Cl. ..................................... 514/452; 549/375; 549/370; 549/362; 549/350; 549/342; 549/332; 514/450
[58] Field of Search .............. 549/375, 370, 362, 350, 549/342, 332; 514/452, 450

[56] References Cited

U.S. PATENT DOCUMENTS 2,500,155 3/1950 Croxall et al. ..................... 549/375
2,992,234 7/1961 Acker et al. ....................... 549/375

FOREIGN PATENT DOCUMENTS 0094239 11/1983 European Pat. Off. ............ 549/375
433392 7/1966 Japan ................................... 549/375
2046733A 11/1980 United Kingdom .

OTHER PUBLICATIONS

J. Fried et al, "Advances in Prostaglandin and Thromboxane Research", vol. 6, pp. 427–436, Raven Press, N.Y., 1980.

Primary Examiner—Nicky Chan
Attorney, Agent, or Firm—Cushman, Darby & Cushman

[57] ABSTRACT

The invention concerns novel [(4-phenyl-1,3-dioxan-cis-5-yl)alkyl]phenylalkanoic acids of the formula I wherein Ra and Rb are a variety of substituents including alkyl, alkenyl, halogenoalkyl, phenyl and benzyl, or together form polymethylene; Rc is hydroxy, alkoxy or alkanesulphonamido; $A^1$ and $A^2$ are polymethylene; X is oxygen, sulphur or a direct bond; and benzene ring A bears a variety of substituents; and, when Rc is hydroxy, the physiologically acceptable salts thereof. The compounds of formula I are thromboxane antagonists of value in treating a variety of disease conditions. The invention also provides processes for the manufacture of, and pharmaceutical compositions of, the compounds of formula I.

10 Claims, No Drawings

[(4-PHENYL-1,3-DIOXAN-CIS-5-YL)ALKYL]-PHENYLALKANOIC ACID DERIVATIVES

This invention concerns phenylalkanoic acid derivatives and, more particularly, novel [(4-phenyl-1,3-dioxan-cis-5-yl)alkyl]phenylalkanoic acid derivatives which antagonise one or more of the actions of thromboxane $A_2$ (hereafter referred to as "TXA$_2$"), and are valuable therapeutic agents.

It is known that TXA$_2$ is a potent aggregator of blood platelets and a powerful vasoconstrictor. TXA$_2$ is also a potent constrictor of bronchial and tracheal smooth muscle. TXA$_2$ may therefore be involved in a wide variety of disease conditions, for example ischaemic heart disease such as myocardial infarction and angina, cerebrovascular disease such as transient cerebral ischaemia, migraine and stroke, peripheral vascular disease such as atherosclerosis, microangiopathy, hypertension and blood clotting defects due to lipid imbalance, and pulmonary disease such as pulmonary embolism, bronchial asthma, bronchitis, pneumonia, dyspnoea and emphysema. Accordingly, compounds which antagonise the actions of TXA$_2$ may be expected to have therapeutic value in the prevention or treatment of any one or more of the above mentioned diseases or any other disease conditions in which it is desirable to antagonise the actions of TXA$_2$.

Certain 4-(hydroxyalkyl)-1,3-dioxan-trans-5-ylalkenoic acids are known (UK patent application No. 8004647, published as Ser.No. 2046733A) as inhibitors of the enzyme responsible for the synthesis of TXA$_2$. In addition, certain 6-(t-butoxyalkynyl)-2,2-dimethyl-1,3-dioxan-cis-4-ylalkenoic acids have been described by Fried and co-workers (*Advances in Prostaglandin and Thromboxane Research*, 1980, 6, 427–43) as inhibitors of various enzymes in the series of biochemical conversions known as the arachidonic acid cascade.

We have now discovered that a series of [1,3-dioxan-5-ylalkyl]phenylalkanoic acids possesses thromboxane antagonist properties and this is the basis for our invention.

According to the invention there is provided a [(4-phenyl-1,3-dioxan-cis-5-yl)alkyl]phenylalkanoic acid derivative of the formula I (hereafter "compound of formula I") wherein Ra and Rb are independently hydrogen, (2–6C)alkenyl, (1–8C)alkyl optionally bearing up to three halogeno substituents, or phenyl or benzyl optionally bearing up to three nuclear substituents selected from halogeno, (1–6C)alkyl, (1–6C)alkoxy, (1–4C)alkylenedioxy, trifluoromethyl, cyano, nitro, hydroxy, (2–6C)alkanoyloxy and (1–6C)alkanoylamino, provided that when Ra and Rb are both other than hydrogen the total number of carbon atoms in Ra and Rb taken together is 8 or less; or Ra and Rb together form (2–7C)polymethylene optionally bearing (1–4C)alkyl; Rc is hydroxy, (1–6C)alkoxy or (1–6C)alkanesulphonamido; A$^1$ and A$^2$ are independently (1–4C)polymethylene optionally bearing a methyl substituent such that the total number of carbon atoms in A$^1$ and A$^2$ taken together is 5 or less; X is oxygen, sulphur or a direct bond; and benzene ring B optionally bears one or two substituents selected from halogeno, (1–6C)alkyl, (1–6C)alkoxy, hydroxy, (2–6C)alkanoyloxy, (1–6C)alkanoylamino, trifluoromethyl and nitro; and the substituents at positions 4 and 5 of the dioxane ring have cis-relative stereochemistry; or for those compounds wherein Rc is hydroxy, a salt thereof with a base affording a physiologically acceptable cation.

It will be appreciated that the compounds of formula I contain at least two asymmetric carbon atoms (i.e. at C$_4$ and C$_5$ of the dioxane ring) and may exist and be isolated in racemic and optically active forms. In addition those compounds of formula I wherein A is vinylene exist, and may be isolated, in separate stereoisomeric forms ('E' and 'Z') about that group. It is to be understood that the present invention encompasses any racemic, optically active or stereoisomeric form (or mixtures thereof) which is capable of antagonising one or more of the actions of TXA$_2$, it being well known in the art how to prepare individual optical isomers (for example by synthesis from optically active starting materials or resolution of a racemic form) and individual 'E' and 'Z' stereoisomers (for example by chromatographic separation of a mixture thereof), and how to determine the TXA$_2$ antagonist properties using the standard test described hereafter.

In this specification, the terms Ra, Rb and Rc etc, are used to depict generic radicals and have no other significance.

A particular value for Ra or Rb when it is (1–8C)alkyl is, for example, methyl, ethyl, propyl, isopropyl, butyl, pentyl, hexyl, heptyl or octyl, and when it is (1–8C)alkyl bearing up to three halogeno atoms is, for example chloromethyl, 2-chloroethyl, trifluoromethyl or 2,2,2-trifluoroethyl.

A particular value for Ra or Rb when it is (2–6C)alkenyl is, for example, vinyl, allyl or 2-methylallyl.

Particular values for substituents, which may be present on benzene ring B or when Ra or Rb is substituted phenyl or benzyl as defined above, are, for example:
for halogeno: fluoro, chloro, bromo or iodo;
for ((1–6C)alkyl: methyl, ethyl, propyl or isopropyl;
for (1–6C)alkoxy: methoxy, ethoxy or propoxy;
for (1–4C)alkylenedioxy: methylenedioxy or ethylenedioxy;
for (1–6C)alkanoylamino: formamido, acetamido or propionamido; and
for (2–6C)alkanoyloxy: acetoxy or propionyloxy.

In general when one of Ra and Rb is hydrogen it is preferred that the other of Ra and Rb is arranged so as to have cis-relative stereochemistry with reference to the substituents at positions 4 and 5 of the dioxane ring.

A particular value for Ra and Rb when together they form (2–7C)polymethylene is, for example, ethylene, trimethylene, tetramethylene, pentamethylene or hexamethylene; and a particular value for an optional (1–4C)alkyl substituent thereon is, for example, methyl.

A particular value for Rc when it is (1–6C)alkanesulphonamido is, for example, methanesulphonamido, ethanesulphonamido, propanesulphonamido or 1-methylethanesulphonamido.

A particular value for Rc when it is (1–6C)alkoxy is, for example, methoxy or ethoxy.

A particular value for A$^1$ or A$^2$ is, for example, methylene, ethylene, trimethylene or tetramethylene.

Specific examples of Ra and Rb are, for example, hydrogen, methyl, ethyl, propyl, isopropyl, butyl, pentyl, hexyl, octyl, vinyl, allyl, 2-methylallyl, trifluoromethyl, chloromethyl, 2-chloroethyl, phenyl optionally bearing a fluoro, chloro, bromo, methyl, methoxy, trifluoromethyl, nitro, hydroxy, cyano, acetamido or methylenedioxy substituent, dichlorophenyl, dimethylphenyl, or benzyl; or are, for example, when they together form trimethylene, pentamethylene or hexamethylene, optionally bearing a methyl substituent.

Specific values for benzene ring B are, for example, when it is phenyl, 2-methylphenyl, 2-ethylphenyl, 2-isopropylphenyl, 2-methoxyphenyl, 2-fluorophenyl, 2-chlorophenyl, 2-bromophenyl, 2-hydroxyphenyl, 2-trifluoromethylphenyl, 3-trifluoromethylphenyl, 3-fluorophenyl, 3-chlorophenyl, 4-fluorophenyl, 4-methylphenyl or 2,6-difluorophenyl.

A preferred value for Rc is, for example, hydroxy, methoxy, ethoxy, methanesulphonamido or ethanesulphonamido, of which hydroxy is especially preferred.

A preferred value for benzene ring B is, for example, when it is unsubstituted; ortho-substituted by fluoro, chloro, methyl, hydroxy, methoxy, ethyl or isopropyl; or meta-substituted by fluoro or chloro.

Specific combinations of Ra and Rb which are preferred are, by way of example,:

(i) Ra and Rb are both hydrogen, methyl, ethyl, propyl, butyl or trifluoromethyl;

(ii) one of Ra is hydrogen and the other is trifluoromethyl, chloromethyl, isopropyl, hexyl, octyl, phenyl (optionally bearing 1 or 2 fluoro, chloro, bromo, methyl, methoxy, trifluoromethyl, hydroxy, cyano or acetamido) or phenyl bearing methylenedioxy; and (iii) Ra and Rb together form trimethylene, tetramethylene, pentamethylene, hexamethylene or a group of the formula: —CH$_2$CH$_2$.CHCH$_3$.CH$_2$CH$_2$—.

Specific preferred values for benzene ring B are, for example, when it is phenyl, or 2-fluoro-, 2-chloro-, 2-bromo-, 2-methyl-, 2-ethyl-, 2-isopropyl-, 2-methoxy-, 2-hydroxy-, 3-fluoro- or 3-chloro-phenyl.

A preferred group of compounds of the invention comprises acids of the formula Ia wherein:

(i) Ra and Rb are both hydrogen, methyl, ethyl, propyl, butyl, or trifluoromethyl;

(ii) or together form trimethylene, tetramethylene, pentamethylene, hexamethylene or a group of the formula: —CH$_2$CH$_2$ . CHCH$_3$.CH$_2$CH$_2$—; or (iii) Ra is (3–8C)alkyl, trifluoromethyl, chloromethyl, 2-chloroethyl, benzyl or phenyl, the last of which may optionally bear 1 or 2 halogeno, (1–4C)alkyl, (1–4C)alkoxy, trifluoromethyl, hydroxy, cyano or (1–4C)alkanoylamino substituents, or a methylenedioxy substituent, and Rb is hydrogen;

benzene ring B is unsubstituted or is 2-halogeno-, 2-(1–4C)alkyl-, 2-(1–4C)alkoxy-, 2-hydroxyor 3-halogeno-phenyl; $A^1$ and $A^2$ have the meanings defined hereinabove; $X^1$ is oxygen or a direct bond; and Ra and the substituents at the 4 and 5-positions of the dioxane ring have cis-relative stereochemistry; or a salt thereof with a base affording a physiologically acceptable cation; or a methyl or ethyl ester thereof; or a methanesulphonamido, ethanesulphonamido or 1-methylethanesulphonamido derivative thereof.

A preferred value for the group $X.A^2$ is, for example ethylene, oxymethylene or trimethylene.

A preferred value for $A^1$ is methylene.

A preferred value for Ra when it is (3–8C)alkyl is, for example, isopropyl, butyl, hexyl or octyl.

Preferred values for substituents on Ra when it is phenyl are, for example:
for halogeno: fluoro, chloro or bromo;
for (1–4C)alkyl: methyl;
for (1–4C)alkoxy: methoxy; and
for (1–4C)alkanoylamino: acetamido.

Preferred values for substituents on benzene ring B are, for example:

for 2-halogeno: 2-fluoro, 2-chloro or 2-bromo;
for 3-halogeno: 3-fluoro or 3-chloro;
for 2-(1–4C)alkyl: 2-methyl, 2-ethyl or 2-isopropyl; and
for 2-(1–4C)alkoxy: 2-methoxy.

Particular salts of compounds of formula I wherein Rc is hydroxy are, for example, alkali metal and alkaline earth metal salts such as lithium, sodium, potassium, magnesium and calcium salts, aluminium and ammonium salts, and salts with organic amines or quaternary bases forming physiologically acceptable cations, such as salts with methylamine, dimethylamine, trimethylamine, ethylenediamine, piperidine, morpholine, pyrrolidine, piperazine, ethanolamine, triethanolamine, N-methylglucamine, tetramethylammonium hydroxide and benzyltrimethylammonium hydroxide.

Specific compounds of the invention are described in the accompanying Examples. Of these, the compound in Example 3 is particularly preferred either in the free acid or salt form.

The compounds of formula I may be manufactured by conventional procedures of organic chemistry well known in the art for the production of analogous compounds. Such processes are provided as a further feature of the invention and are illustrated by the following preferred procedures in which Ra, Rb, Rc, benzene ring B, $A^1$, $A^2$ and X have any of the meanings defined hereinbefore:

(a) For a compound wherein Rc is hydroxy, hydrolysing an acid derivative of the formula II wherein Q is cyano, carbamoyl, alkoxycarbonyl, phenoxycarbonyl or benzyloxycarbonyl.

A preferred value for W is, for example, cyano.

The hydrolysis is conveniently carried out under the influence of base, for example an alkali metal hydroxide (such as sodium or potassium hydroxide) in a suitable aqueous solvent, for example a (1–4C)alkanol (such as methanol or ethanol) or a glycol (such as ethylene glycol) at a temperature in the range, for example, 15° to 160° C. In general, higher reaction temperatures are required when W is cyano or carbamoyl, for example in the range 80°–160° C.

The starting materials of formula II may be obtained by standard procedures of organic chemistry. For example, those compounds of formula II wherein Q is cyano may be obtained as shown in Scheme I hereafter, and may be converted to the remaining starting materials of formula II by standard procedures.

(b) For a compound of formula I wherein Rc is hydroxy, oxidising an alcohol of the formula III wherein Xa is oxygen or a direct bond.

A range of oxidising agents is suitable for use in this process, for example, platinum and oxygen in aqueous acetone or tetrahydrofuran; or alkaline persulphate in the presence of ruthenium trichloride. A suitable solvent or diluent which is compatible with the oxidising agent may conveniently be employed.

The process may be carried out at a temperature in the range, for example 10° to 50° C., but is preferably performed at or near room temperature in order to minimise the risk of oxidation of other sensitive substituents in the molecule. Equally, where such substituents are present, the process may be conveniently performed in two steps using two oxidising agents, that is by intermediate formation of the corresponding aldehyde of the formula IV using an oxidising agent such as pyridinium chlorochromate (preferably in a solvent such as dichloromethane), or the Pfitzner-Moffatt reagent (dicyclohexylcarbodiimide and dimethyl sulphoxide in the presence of an acid catalyst for example pyridinium trifluoroacetate), in both cases at or near room temperature. The aldehyde of formula IV may then be separately oxidised to the required carboxylic acid of formula I (Rc=OH) by reaction with a mild oxidising agent such as silver oxide in the presence of an alkali metal hydride such as sodium hydroxide, conveniently in a solvent or diluent, for example a (1–4C)alkanol such as ethanol, and at or near room temperature. This latter process is also provided as a feature of the invention.

The starting materials of formula III and IV may be obtained by standard procedures of organic chemistry, for example as illustrated in Scheme II hereafter.

(c) Reacting an erythro-diol derivative of the formula V wherein one of Rd and Re is hydrogen and the other is hydrogen, alkanesulphonyl, arenesulphonyl or a group of the formula —CRR$^1$.OH wherein R and R$^1$ are the same or different alkyl, with a carbonyl compound of the formula RaRb.CO, or an acetal, hemiacetal or hydrate thereof.

A suitable value for Rd or Re when it is alkanesulphonyl is, for example, methanesulphonyl or ethanesulphonyl and when it is arenesulphonyl is, for example, benzenesulphonyl or p-toluenesulphonyl. A suitable value for R or R$^1$ is, for example, methyl or ethyl.

The carbonyl compound of the formula RaRb.CO (or its hydrate, or its acetal or hemiacetal with a (1–4C)alkanol) is preferably used in excess.

Depending on the nature of Rd and Re different reaction conditions are necessary. Thus, when Rd and Re are both hydrogen or when one is a group of the formula —CRR$^1$.OH and the other is hydrogen, the reaction is carried out in the presence of an acid catalyst, for example, hydrogen chloride, hydrogen bromide, sulphuric acid, phosphoric acid, p-toluenesulphonic acid or the anionic form of a sulphonated polystyrene catalyst, conveniently in a suitable solvent or diluent, for example an ether such as diethyl ether, dibutyl ether, 1,2-dimethoxyethane or tetrahydrofuran, and at a temperature in the range, for example, 10° to 120° C. The acid catalyst may also be provided by the inherent acidity of those starting materials of formula V wherein Rc is hydroxy.

Similarly, when one of Rd and Re is alkanesulphonyl or arenesulphonyl and the other is hydrogen, the reaction is carried out first in the presence of an acid catalyst, for example under the conditions described above to produce an intermediate of the formula V, wherein one of Rd and Re is alkanesulphonyl or arenesulphonyl, and the other is a group of the formula —CRaRb.OH. The latter intermediate may then be cyclised in situ to the required compound of formula I by addition of a strong base, for example, sodium hydride or butyllithium, in a suitable solvent or diluent, for example in the ether solvent used for the acid catalysed step above, and at a temperature in the range, for example, 30°–100° C. It will be appreciated that the above mentioned intermediate may also be isolated, characterised and separately cyclised under the influence of strong base to give a compound of formula I. Such a procedure is encompassed by the invention.

Those starting materials of formula V wherein Rd and Re are both hydrogen may be obtained by mild hydrolysis or alcoholysis of the dioxane ring of a compound of formula I, for example, in which Ra and Rb are both methyl or ethyl radicals, obtained by another process described herein. This reaction will normally be carried out at a temperature in the range, for example, 25°–100° C. and preferably in the range 30°–60° C., using an aqueous mineral acid such as hydrochloric acid in an alcoholic solvent such as ethanol or 2-propanol. Those starting materials of formula V wherein one of Rd and Re is a group of the formula —CRR$^1$.OH and the other is hydrogen, are generally obtained as intermediates in the above mentioned formation of the erythro- diol of formula V (Rd=Re=H) and are not normally isolated or characterised. Accordingly, the invention also provides a process which comprises reacting a compound of formula I for example wherein Ra and Rb are methyl or ethyl, with an excess of a compound of the formula RaRb.CO in the presence of an acid-catalyst (such as those mentioned above), conveniently in a suitable solvent or diluent (such as an ether mentioned above) and at a temperature in the range for example 10° to 120° C.

Those starting materials of formula V wherein one of Rd and Re is alkanesulphonyl or arenesulphonyl and the other is hydrogen, may be obtained from the corresponding erythro-diol of formula V (Rd=Re=H) by reaction with one molecular equivalent of the appropriate alkanesulphonyl or arenesulphonyl halide, for example methanesulphonyl chloride or p-toluenesulphonyl chloride, in a suitable solvent or diluent (such as an ether or dichloromethane) and in the presence of a base such as pyridine or triethylamine.

Process (c) is not normally suitable for the production of compounds of formula I wherein both Ra and Rb are trifluoromethyl.

Under some circumstances when Rc is hydroxy in the starting materials of formula V, some degree of reaction at the carboxylic acid moiety may occur during process (c) such that hydrolysis [according to process (a) hereinbefore] of the reaction product may be necessary in order to obtain the required compound of formula I wherein Rc is hydroxy.

The necessary starting ketones of formula RaRb.CO and their derivatives are generally already known or may readily be obtained by standard techniques or organic chemistry.

(d) For a compound of formula I wherein Ra, Rb or benzene ring B bears a hydroxy substituent, deprotecting a corresponding derivative of said compound wherein the hydroxy substituent is protected by a trimethylsilyl, (1–6C)alkyl (such as methyl or ethyl) or acyl (such as acetyl or benzoyl protecting group.

The deprotection conditions required necessarily depend on the protecting groups concerned. Thus, for example, when it is methyl or ethyl (i.e. the starting material is the corresponding methoxy or ethoxy compound of formula I) the deprotection may be carried out, for example, by heating with sodium thioethoxide in a suitable solvent (such as N,N-dimethylformamide) at an elevated temperature, for example 90°–160° C. Similarly, when the protecting group is acyl, it may be removed, for example by hydrolysis in the presence of a base (such as sodium or potassium hydroxide) in a suitable aqueous solvent [such as a (1–4C)alkanol or a glycol] at a temperature in the range, for example, 10°–60° C. Similarly in the case of a trimethylsilyl protecting group, it may be removed for example, by reaction with aqueous tetrabutylammonium fluoride or sodium fluoride in conventional manner.

The necessary protected derivatives of the formula I compounds may be made by analogy with the other processes described herein.

(e) For a compound of formula I wherein Ra and Rb are both hydrogen, reacting an erythro-diol of the formula V wherein Rd and Re are both hydrogen, with methylene bromide in the presence of base.

A particularly suitable base is for example, sodium or potassium hydroxide, or sodium hydride The process is preferably carried out in a suitable solvent or diluent, for example dimethyl sulphoxide, and at a temperature in the range, for example, 10° to 40° C., conveniently at or near room temperature.

When a compound of formula I wherein Rc is (1–6C-)alkoxy is required, the corresponding acid of formula I wherein Rc is hydroxy, or a reactive derivative thereof, is esterified using a conventional procedure.

Thus, for example, a compound of formula I wherein Rc is hydroxy (hereafter an acid of formula I) , or a reactive derivative thereof, may be esterified by reaction with the appropriate (1–6C)alkanol.

It will be appreciated that when a free acid of formula I is used in the process, water is produced during the reaction Consequently, in such cases it is particularly convenient to perform the process in the presence of a suitable dehydrating agent, for example dicyclohexylcarbodiimide, in the presence of a suitable solvent or diluent for example tetrahydrofuran, acetone, methylene chloride or 1,2-dimethoxyethane, at a temperature in the range, for example, 10° to 50° C., but preferably at or near room temperature.

A suitable reactive derivative of an acid of formula I is, for example, an acid chloride, bromide, anhydride, mixed anhydride with formic acid, or an azide, which may be produced from the free acid in conventional manner. When such a derivative is used in the process, no additional dehydrating agent is necessary, and the (1–6C)alkanol is conveniently used in large excess, optionally diluted with a suitable diluent or solvent such as an ether, for example tetrahydrofuran or 1,2-dimethoxyethane.

In general, when a reactive derivative of an acid of formula I is used no external heating of the reaction is necessary.

When a compound of formula I wherein Rc is (1–6C-)alkanesulphonamido is required, a corresponding acid of formula I, or a reactive derivative thereof, is reacted with the appropriate (1–6C)alkanesulphonamide.

Thus, for example a free acid of formula I may be reacted with a suitable dehydrating agent, for example dicyclohexylcarbodiimide, optionally together with an organic base, for example 4-dimethylaminopyridine, with a (1–6C)alkanesulphonamide in the presence of a suitable solvent or diluent, for example methylene chloride at a temperature in the range, 10° to 50° C., but preferably at or near room temperature Alternatively, a reactive derivative of an acid of formula I, for example an acid halide (such as the acid chloride), may be reacted with an alkali metal salt (such as the sodium salt) of the appropriate (1–6C)alkanesulphonamide, conveniently at or near room temperature and in a suitable solvent or diluent, for example an ether, N,N-dimethylformamide or methylene chloride.

When a salt of an acid of formula I is required, it is obtained by reaction with the appropriate base affording a physiologically acceptable cation, or by any other conventional procedure.

Further, when an optically active form of a compound of formula I is required, one of the aforesaid processes is carried out using optically active starting material. Alternatively, when Rc is hydroxy, a racemic form of the said compound may be reacted with an optically active form of a suitable organic base, for example ephedrine, N,N,N-trimethyl(1-phenylethyl)ammonium hydroxide or 1-phenylethylamine, followed by conventional separation of the diastereoisomeric mixture of salts thus obtained, for example by fractional crystallisation from a suitable solvent, for example a (1–4C)alkanol, whereafter the optically active form of said compound of formula I may be liberated by treatment with acid using a conventional procedure for example using an aqueous mineral acid such as dilute hydrochloric acid.

When an optically active form of a compound of formula I wherein Rc is other than hydroxy is required, it may be obtained using the aforementioned esterification or amidification procedures using the appropriate optically active form of said acid.

Many of the intermediates defined herein are novel and are provided as further separate features of the invention As stated earlier, the compounds of formula I are antagonists of one or more of the actions of $TXA_2$, for example certain of its actions on blood platelets, the vasculature and/or the lung. The antagonism may be demonstrated in one or other of the following standard tests:

(a) The rabbit aortal strip model devised by Piper and Vane (*Nature*, 1969, 223, 29–35) using as agonist the $TXA_2$ mimetic agent known as U46619 (R. L. Jones et alia in "Chemistry, Biochemistry and Pharmacological Activity of Prostanoids", eds. S. M. Roberts and F. Scheinmann, at p. 211; Pergamon Press, 1979);

(b) a blood platelet aggregation test based on that described by Born (*Nature*, 1962, 194, 927–929) and involving measuring the inhibition by a test compound of aggregation of citrated, platelet rich human plasma induced by a sub-maximal concentration (in the range 50–250 ng./ml.) of U46619; and (c) a bronchoconstriction test involving measuring the inhibition by a test compound of the bronchoconstriction induced in the Konzett-Rossler guinea-pig model (as modified by Collier and James, *Brit. J. Pharmacol.*, 1967, 30, 283–307) by intravenous administration of the $TXA_2$ mimetic agent, U46619 at 1–1.5 μg/kg.

Similarly, the antagonism of the effects of $TXA_2$ on the vasculature may be demonstrated in the following manner:

(d) Male rats (Alderley Park strain) are anaesthetised with sodium pentobarbital and blood pressure is monitored at the carotid artery. The $TXA_2$ mimetic agent U46619 is administered intravenously via the jugular vein and an $ED_{50}$ (dose necessary to produce 50% of the maximum hypertensive effect) is established (n=3). The $ED_{50}$ for U46619 is approximately 5 μg/kg. A test compound is then administered either intravenously via the jugular vein or orally via a cannula directly into the stomach and the animal challenged with an $ED_{50}$ dose of U46619, five minutes after dosing with test compound and then successively every ten minutes until the hypertensive effect of U46619 is no longer blocked.

In general, compounds of formula I show significant activity in one or more of the above tests without any sign of overt toxicity at the active dose in tests (c) or (d). By way of example, the compound of formula I described in Example 3 hereinafter gives a $pA_2$ of 6.19 in test (a).

As stated previously, the compounds of formula I may be used in the therapy or prevention of diseases or adverse conditions in warm-blooded animals in which it is desirable to antagonise one or more of the actions of TXA$_2$. In general, a compound of formula I will be administered for this purpose by an oral, rectal, intravenous, subcutaneous, intramuscular or inhalation route, so that a dose in the range, for example 0.5–20 mg/kg. body weight, will be given up to four times per day, varying with the route of administration, the severity of the condition and the size and age of the patient under treatment.

The compounds of formula I will generally be used in the form of a pharmaceutical composition comprising a compound of formula I or, where appropriate, a salt thereof as defined hereinbefore, together with a pharmaceutically acceptable diluent or carrier. Such compositions are provided as a further feature of the invention and may be in a variety of dosage forms. For example, they may be in the form of tablets, capsules, solutions or suspensions for oral administration; in the form of suppositories for rectal administration; in the form of sterile solutions or suspensions for administration by intravenous or intramuscular injection; in the form of aerosols or nebuliser solutions or suspensions for administration by inhalation; and in the form of powders together with pharmaceutically acceptable inert solid diluents such as lactose for administration by insufflation.

The pharmaceutical compositions may be obtained by conventional procedures using pharmaceutically acceptable diluents and carriers well known in the art. Tablets and capsules for oral administration may conveniently be formed with an enteric coating, for example comprising cellulose acetate phthalate, to minimise contact of the active ingredient of formula I with stomach acids.

The pharmaceutical compositions of the invention may also contain one or more agents known to be of value in diseases or conditions intended to be treated; for example, a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an antihistamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

In addition to their use in therapeutic medicine the compounds of formula I are also useful as pharmacological tools in the development and standardisation of test systems for the evaluation of the effects of TXA$_2$ in laboratory animals such as cats, dogs, rabbits, monkeys, rats, and mice, as part of the search for new therapeutic agents. The compounds of formula I may also be used because of their TXA$_2$ antagonist properties in helping to maintain the viability of blood and blood vessels in warm-blooded animals (or parts thereof) under-going artificial extracorporeal circulation, for example during limb or organ transplants. When used for this purpose a compound of formula I or a physiologically acceptable salt thereof will generally be administered so that a steady state concentration in the range, for example, 0.5 to 50 mg. per liter is achieved in the blood.

The invention will now be illustrated in the following non-limiting Examples in which, unless otherwise stated:

(i) evaporations were carried out by rotary evaporation in vacuo;

(ii) operations were carried out at room temperature, that is in the range 18°–26° C.;

(iii) column chromatography was performed on Merck Kieselgel 60 (Art, 7734) using approximately 50–70 g. of SiO$_2$ per g. of sample, and monitoring the process by thin layer chromatography on Merck 0.25 mm. Kieselgel 60F 254 plates (Art. 5715); flash chromatography was performed in Merck Kieselgel (Art 9385); these materials were obtained from E. Merck, Darmstadt, W. Germany;

(iv) yields are given for illustration only and are not necessarily the maximum attainable;

(v) NMR spectra were normally determined at 90 MHz in CDCl$_3$ using tetramethylsilane (TMS) as an internal standard, and expressed as chemical shifts (delta values) relative to TMS using the following abbreviations for designation of major peaks: s, singlet; m, multiplet; t, triplet; br, broad; d,doublet; when a single chemical shift value is given for a multiplet (m) this corresponds to the centre point of the signals making up the multiplet; and (vi) end-products were isolated as racemates, and characterised by NMR and mass spectroscopy and other standard procedures; and (vii) the following abbreviations are used ; DMF: N,N-dimethylformamide; DMSO: dimethylsulphoxide; DMPU: N,N-dimethylpropyleneurea; THF: tetrahydrofuran; and petroleum ether (b.p. 40°–60° C. is referred to as "petrol (40°–60° C.)" and other fractions by analogy.

EXAMPLE 1

4-(o-[2,2-Dimethyl-4-phenyl-1,3-dioxan-cis-5-ylmethyl]phenyl)butyronitrile (1.48 g.) was added to a solution of potassium hydroxide (0.84 g.) in 1,2-ethanediol (40 ml.) and the stirred mixture was heated at 140°–150° C. for 18 hours. After cooling, the mixture was diluted with water (100 ml.) and extracted with ether (2×50 ml.). The aqueous phase was acidified to pH5 (2M HCl) and extracted with ethyl acetate (3×100 ml.). The combined ethyl acetate extracts were washed with saturated brine (50 ml.), dried, (MgSO$_4$) and concentrated to give a brown oil (1.5 g.) which was purified by flash column chromatography, eluting with petrol (60°–80° )/ethyl acetate/acetic acid (50:50:2,v/v), to give 4-(o-[2,2-dimethyl-4-phenyl-1,3-dioxan-cis-5-ylmethyl]phenyl)-butanoic acid (1.15 g.) as an oil; NMR :1.56 (3H,s), 1.60(3H,s), 1.5–3.1 (9H,m), 3.5–4.1 (2H,m), 5.25 (1H,d J=2Hz) and 7.0–7.6 (9H,m)ppm; m/e: 386 (M$^+$+NH$_4$), 369 (M$^+$+H) 328 (M$^+$+NH$_4$—CO), 298 (C$_{19}$H$_{20}$O$_2$.NH$_4$$^+$).

The starting material was obtained as follows:

(i) A stirred solution of sodium ethoxide (from 0.53 g. sodium) in ethanol (80 ml.) was treated with ethyl benzoylacetate (4.42 g.). After 1 hour, -(o-chloromethylphenyl)propyl chloride (4.57 g.) was added and stirring was continued for 24 hours. The mixture was then diluted with ether (100 ml.) and water (100 ml.). The organic layer was separated, washed with saturated brine (50 ml.), dried (MgSO$_4$) and evaporated to give ethyl 2-benzoyl-3-(o-(3-chloropropyl)phenyl]propanoate (A) as a yellow oil (7.66 g.), NMR: 1.1 (3H,t), 2.1 (2H,m), 2.7–3.7 (6H,m), 4.1 (2H,m), 4.65 (1H,t) and 7.0–8.2 (9H,m)ppm, which was used without further purification.

(ii) A suspension of sodium borohydride (1.27 g.) in dry THF (200 ml.) was treated with anhydrous zinc chloride (2.28 g.) with stirring under argon. After 30 minutes a solution of (A) (6.0 g.) in THF (50 ml.) was added and stirring was continued for 20 hours. The mixture was then treated with aqueous acetic acid (20% v/v, 30 ml.), water (100 ml.) and ethyl acetate (100 ml.), and the organic layer was separated. Washing with saturated brine (100 ml.), drying (MgSO$_4$) and evaporation gave an oil which on flash column chromatography, eluting with chloroform/hexane (7/3, v/v) gave the errythro-isomer of ethyl 3-[o-(3-chloropropyl)-phenyl)]-2-α-hydroxybenzylpropanoate (B) as an oil (3.5 g.), NMR: 0.9 (3H,t), 1.9 (2H,m), 2.4 (2H,m), 2.7–3.1 (3H,m), 3.4(2H,t), 3.9 (2H,q), 5.1 (1H,d) and 7.0–7.5(9H,m)ppm.

(iii) A solution of (B) (3.5 g.) in ether (30 ml.) was added to a stirred suspension of lithium aluminium hydride (0.37 g.) in ether (120 ml.) at −70° C. under argon. After 15 minutes, the mixture was allowed to warm to room temperature and stirring was continued overnight. The mixture was then cooled to 0° C. and treated sequentially with ethyl acetate (20 ml.) and saturated aqueous ammonium chloride solution (20 ml.). The resultant precipitate was removed by filtration The separated organic layer was washed with saturated brine (30 ml.), dried (MgSO$_4$) and evaporated. The residue was purified by flash column chromatography eluting with petrol (40–60° /ethyl acetate (55/45 v/v ) to give erythro-3-[o-(3 chloropropyl)phenyl]-2-α-hydroxy.benzylpropanol (C) as a colourless oil which solidified on standing to give a solid (2.44 g.) of low melting point (iv) A mixture of (C) (2.44 g.), 2,2-dimethoxypropane (25 ml.) and p-toluenesulphonic acid (10 mg.) was allowed to stand overnight Ether (100 ml.) and water (100 ml.) were added and the aqueous layer was The combined ether extracts were dried (MgSO$_4$) and evaporated to give (4,5-cis-)-5-[o-(3-chloropropyl)benzyl]-2,2-dimethyl-4-phenyl-1,3-dioxane(D) (2.62 g.) as a colourless oil, NMR: 1.6 (3H,s), 1.65 (3H,s), 1.7–3.0 (7H,m), 3.35 (2H,m), 3.5–4.2 (2H,m), 5.3 (1H,d) and 7.0–7.6 (9H,m)ppm, which oil was used without purification.

(v) A stirred solution of potassium cyanide (0.43 g.) in dry DMSO (60 ml.) was treated with a solution of (D) (2.36 g.) in dry DMSO (20 ml.) and the mixture was heated at 70°–80° C. for 7 hours. Water (100 ml.) and ethyl acetate (100 ml.) were added to the cooled solution and the two layers were separated. The aqueous layer was extracted with ethyl acetate (100 ml.), then the combined extracts were washed with saturated brine (2×50 ml.), dried (MgSO$_4$) and evaporated to give a yellow oil. Flash column chromatography, eluting with petrol (60°–80°) ethyl acetate (80:20 v/v) gave 4-(o-[2,2-dimethyl-4phenyl 1,3-dioxan-cis-5-ylmethyl]-phenylbutyronitrile (1.83 g.) as a colourless oil which solidified on standing to give a solid of low melting point; NMR: 1.45 (3H,s), 1.5 (3H,s), 1.5–3.2 (9H,m), 3.4–4.2 (2H,m), 5.2 (1H,d) and 6.9–7.4 (9H,m)ppm.

EXAMPLE 2

A suspension of finely-divided platinum (prepared by hydrogenation of Adams catalyst [1.54 g.] in pentane) in water (150 ml.) was treated sequentially with a solution of 2-(m-[2,2-dimethyl-4-phenyl-1,3-cis- -5-ylmethyl]-phenoxy)ethanol (220 mg.) in aqueous acetone (15 ml, 65% v/v acetone) and powdered sodium bicarbonate (0.53 g.). Oxygen gas was passed through the mixture which was maintained at 55°–60° C. until no starting material could be detected by thin layer chromatography (TLC) (about 2 hours). The platinum was removed by filtration. The aqueous filtrate was acidified to pH5 (0.2 M HCl) and extracted with ethyl acetate (4×100 ml.). The combined extracts were washed with saturated brine (100 ml.), dried (MgSO$_4$) and evaporated to give an oil which was purified by flash column chromatography, eluting with toluene/ethyl acetate/acetic acid (80:20:2 v/v/v), to give m-(2,2-dimethyl-4 phenyl-1,3 dioxan cis-5-ylmethyl)phenoxyacetic acid (146 mg.) as a colourless oil; NMR: 1.56 (3H,s), 1.60 (3H,s), 1.5–2.5 (1H,m), 2.6–2.9 (2H,m), 3.9–4.2 (2H,m), 4.6 (2H,s), 5.27 (1H,d, J=2Hz) and 6.5–7.5 (9H,m)ppm; m/e: 356 (M+), 192 (C$_{11}$H$_{12}$O$_3$+).

The starting material was obtained as follows: (a) A solution containing m-hydroxybenzaldehyde (24.6 g.) and sodium hydroxide (8 g.) in water (250 ml.) was treated with a solution prepared from chloroacetic acid (37.7 g.) and sodium hydroxide (16 g.) in water (100 ml.). The mixture was heated under reflux for 4 hours, cooled to room temperature and acidified to pH2 (2M HCl). The acid mixture was extracted with ether (2×100 ml.). The combined extracts were washed with saturated brine (100 ml.), dried (MgSO$_4$) and evaporated to give a pale brown solid which was redissolved in saturated aqueous sodium hydrogen carbonate solution. The solution was washed with ether to remove neutral impurities, acidified to pH 2 (2M HCl) and extracted with dichloromethane (2×100 ml.). The extracts were washed with brine (100 ml.) dried (MgSO$_4$) and evaporated to give an off-white solid, which was recrystallised from water to give 3-formylphenoxyacetic acid (5.9 g.) NMR: 4.7 (2H,s), 7.1–7.6 (4H,m), 10.0 (1H,s) and 10.9 (1H,br s)ppm.

(b) A solution of 3-formylphenoxyacetic acid (5.0g.) in ethanol (50 ml.) was added to a suspension of sodium borohydride (2.11 g.) in ethanol (100 ml.) with stirring. After 2 hours the reaction was quenched with acetic acid (20%, 50 ml.) and the bulk of the solvent was evaporated. Water (50 ml.) was added and the aqueous mixture was extracted with ethyl acetate (2×100 ml.). The combined extracts were washed with saturated brine (100 ml.), dried (MgSO$_4$) and evaporated to give 3-(hydroxymethyl)phenoxyacetic acid (4.66 g.) as an off white solid, NMR: 4.5(2H,s), 4.65 (2H,s) and 6.6–7.4 (4H,m)ppm, which was used without further purification.

(c) A solution of 3-(hydroxymethyl)phenoxyacetic acid (3.18 g.) in ethanol (30 ml.) was treated with concentrated sulphuric acid (10 drops) and allowed to stand for 3 days. Chloroform (100 ml.) and water (50 ml.) were then added. The organic phase was separated, washed sequentially with saturated aqueous sodium hydrogen carbonate solution (2×50 ml.), water (50 ml.) and saturated brine (50 ml.) and then dried (MgSO$_4$) The dried solution was evaporated and the residue purified by flash column chromatography, eluting with petrol (40°–60° )/ ethyl acetate (60:40 v/v) to give ethyl 3-(hydroxymethyl)phenoxyacetate (2.6 g.) as a colourless oil, NMR: 1.25 (3H,t), 2.8 (1H,br s), 4.25 (2H,q), 4.6 (4H,s) and 6.6–7.4 (4H,m)ppm.

(d) A solution containing ethyl 3-(hydroxymethyl)-phenoxyacetate (2.6 g.) and carbon tetrabromide (8.3 g.) in DMF (30 ml.) was treated with a solution of triphenylphosphine (6.55 g.) in DMF (20 ml.) with stirring. The temperature was maintained below 15° C. during the addition using an ice bath. After 1 hour the mixture was poured into ice-water (300 ml.) and the aqueous mixture was extracted with ether (3×100 ml.). The combined extracts were washed with water (3×100 ml.) and saturated brine (100 ml.), dried (MgSO$_4$) and concentrated. The resultant oil was purified by flash column chromatography, eluting with petrol (60°–80° )/ether (80:20 v/v) to give ethyl 3 (bromomethyl)phenoxyacetate (2.4 g.) as a colourless oil, NMR: 1.3 (3H,t), 4.25 (2H,q), 4.4 (2H,s), 4.6 (2H,s) and 6.7–7.4 (4H,m)ppm.

(e) Using a similar procedure to that used for starting material A in Example 1, but using ethyl 3-(bromomethyl)phenoxyacetate instead of 3-(o-chloromethylphenyl)propylchloride there was obtained ethyl 2-benzoyl-3-[m-(2-ethoxycarbonylethoxy)phenyl]propanoate (E) which was purified by flash column chromatography, eluting with ethyl acetate/hexane (30:70 v/v) giving the product as a colourless oil (2.1 g.); NMR: 1.1(3H,t), 1.25(3H,t), 3.3 (2H,d), 3.9–4.8 (5H,m), 4.5 (2H,s) and 6.5–8.1 (9H,m)ppm.

(f) Similarly, using an analogous sequence of procedures to those described in Example 1 for converting A to D the following intermediates were obtained in converting E to H:

(i) erythro-isomer of ethyl 3-[m-(2-ethoxycarbonylethoxy)phenyl]-2-α-hydroxybenzylpropanoate (F), obtained as an oil (506 mg.) after purification by flash column chromatography eluting with ethyl acetate/hexane (25:75, v/v); NMR : 0.95 (3H,t), 1.3 (3H,t), 2.8–3.2 (3H,m), 3.9 (2H,q ), 4.3 (2H,q), 4.55 (2H,s), 5.0–5.1 (1H,br s) and 6.5–7.5 (9H,m)ppm; m/e: 404 (M+NH$_4$)+; starting from (E) (988 mg.)

(ii) erythro 3-[m-(2-hydroxyethoxyphenyl]-2-α-hydroxybenzylpropanol (G), obtained as a colourless oil (530 mg.); NMR 1.8–2.7 (5H,m), 3.5–4.2 (6H,m), 5.06 (1H,d) and 6.5–7.5 (9H,m)ppm; starting from (F) (720 mg.). [N.B. The ethoxycarbonyl group is reduced during this procedure.]

(iii) (4,5-cis) 5-[m-(5,5-dimethyl-1,4,6-trioxaheptyl) 2,2 -dimethyl-4-phenyl-1,3-dioxane (H), obtained as a colourless oil (422 mg.) after purification by flash column chromatography eluting with petrol (40°–60° )/ethyl acetate (85:15 v/v); NMR: 1.56 (3H,s), 1.58 (3H,s), 1.5–3.0 (3H,m), 3.18 (3H,s), 3.5–4.2 (6H,m), 5.26 (1H,d) and 6.5–7.5 (9H,m)ppm; m/e: 414 (M+); starting from (G) (510 mg.).

(g) A solution of (H) (323 mg.) in dry tetrahydrofuran (THF) (10 ml.) was treated first with a solution containing water (14 microlitres) in dry THF (86 microlitres) and then with p-toluene sulphonic acid (1 mg.). After 40 minutes the solvent was evaporated and the residue was purified by flash column chromatography, eluting with petrol (40°–60° )/ethyl acetate (75/25 v/v) to give 2-(m-2,2-dimethyl-4-phenyl-1,3-dioxan-cis-5-ylmethyl]phenoxy)ethanol (226 mg.) as a colourless oil; NMR: 1.54 (3H,s), 1.57 (3H,s), 1.5–3.0 (3H,m), 3.5–4.2 (6H,m), 5.25 (1H,d): and 6.5–7.5 (9H,m)ppm; m/e: 342 (M+).

EXAMPLE 3

Ethane thiol (0.19 ml.) was added to a stirred suspension of sodium hydride (125 mg., 50% w/w dispersion in mineral oil) and DMPU (7 ml.) at 0° C. under argon. After 30 minutes a solution of 4-(o-[2,2-dimethyl-4-o-methoxyphenyl-1,3-dioxan-cis-5-ylmethyl]phenyl)-butanoic acid (170 mg.) in DMPU (3 ml.) was added and the mixture was heated at 140° C. for 3 hours. The cooled mixture was poured into ice water (30 ml.) and extracted with dichloromethane (3×10 ml.). The aqueous phase was acidified to pH 5 using acetic acid and extracted with ethyl acetate (3×10 ml.). The combined extracts were washed with saturated brine (25 ml.), dried (MgSO$_4$) and evaporated to give an oil. This was purified by flash column chromatography, eluting with toluene/ethyl acetate/acetic acid (80:20:2 v/v) to give 4-(o-[2,2-dimethyl-4-o-hydroxyphenyl-1,3 dioxan cis-5-ylmethyl]phenyl)butanoic acid (52 mg.) as a colourless oil; NMR: 1.55 (3H,s), 1.58 (3H,s), 1.6–3.2 (9H,m), 3.5–4.1 (2H,m), 5.5 (1H,d) and 6.8–7.3 (8H,m)ppm; m/e: 402 (M +NH4)+, 385 (M+H)+, 367 (M+H—H$_2$O)+, 344 (H+NH$_4$—Me$_2$CO)+.

EXAMPLE 4

Using a similar procedure to that used in Example 1, but starting from 4-(o-[2,2-dimethyl-4-o-methoxyphenyl-1,3-dioxan-cis-5-ylmethyl]phenyl)butyronitrile (N) instead of 4-(o-[2,2,-dimethyl-4-phenyl-1,3-dioxan-cis-5-ylmethyl]phenyl)butyronitrile, there was obtained 4-(o-[2,2-dimethyl4-o-methoxyphenyl-1,3-dioxan-cis-5-ylmethyl]phenyl)butanoic acid as an oil (170 mg.) after flash column chromatography, eluting with petrol (60–80° )/ethyl acetate/acetic acid (75:25:2, v/v ; NMR : 1.6 (6H,s), 1.6–3.2 (9H,m), 3.5–4.2 (2H,m), 3.8 (3H,s), 5.5(1H,d) and 6.8–7.6 (8H,m).

The starting butyronitrile derivative (N) was obtained using an analogous sequence of reactions to those described in (i)–(v) of Example 1, starting from ethyl o-methoxybenzoylacetate instead of ethyl benzoylacetate. The following intermediates were isolated:

(i) ethyl 2-(o methoxybenzoyl)-3-[o-(3-chloropropyl)-phenyl]propanoate (J), isolated as a colourless oil NMR: 1.1 (3H,t), 2.1 (2H,m) 2.7–3.7 (6H,m), 3.8 (3H,s), 4.1 (2H,q), 4.7 (1H,t) and 6.8–7.8 (8H,m)ppm;

(ii) erythro-isomer of ethyl 3-[o-(3-chloropropyl)-phenyl]-2-(o-methoxyphenylhydroxymethyl)propanoate (K), obtained as an oil after purification by flash column chromatography, eluting with ethyl acetate/-toluene (4:96, v/v); NMR: 0.9 (3H,t), 1.9 (2H,m), 2.5 (2H,m), 2 7–3.1 (3H,m), 3.4 (2H,t), 3.9 (3H,s and 2H,q), 5.1 (1H,d) and 6.8–7.5 (8H,m) ppm;

(iii) erythro-3-[o-(3-chloropropyl)phenyl]-2-(o-methoxyphenylhydroxymethyl)propanol (L), isolated as a colourless oil, which solidified to give a solid of low melting point after flash column chromatography, eluting with petrol (60°–80° )/ethyl acetate (70:30 v/v); NMR: 1.7–2.9 (7H,m), 3.3 (2H,m), 3.7 (2H,m), 3.8 (3H,s), 5.4 (1H,d) and 6.8–7.6 (8H,m)ppm;

(iv) (4,5-cis-)-5-[o-(3-chloropropyl)benzyl]-2,2-dimethyl-4-o-methoxyphenyl-1,3-dioxane (M), obtained as a colourless oil which solidified on standing to give a white solid (491 mg.) of low melting point after flash column chromatography, eluting with petrol (40–60° )/ethyl acetate (95:5, v/v); NMR: 1.6 (6H,s), 1.7–2.9 (7H,m), 3.3 (2H,m), 3.5–4.2 (2H,m), 3.8 (3H,s), 5.5 (1H,d) and 6.8–7.6 (8H,m)ppm; and (v) 4-(o-[2,2-dimethyl-4-o-methoxyphenyl-1,3-dioxan-cis-5-ylmethyl]phenyl)butyronitrile (N), obtained as an oil which solidified on standing to give a white solid of low melting point after flash column chromatography, eluting with petrol (60°–80°)methyl acetate (80:20 v/v); NMR: 1.6 (6H,s), 1.8–3.1 (9H,m), 3.5–4.1 (2H,m), 3.8 (3H,s), 5.5 (1H,d) and 6.8–7.6 (8H,m)ppm.

EXAMPLE 5

A solution of 3-(m-[2,2-dimethyl-4-phenyl-1,3-dioxan-cis-5-ylmethyl]phenyl)propanol (X) (0.82 g.) in a mixture of water (10 ml.) and acetone (15 ml.) was added to a suspension of platinum [freshly prepared by hydrogenation of Adams catalyst (3.5 g.) in pentane, followed by decantation of the pentane]in water (500 ml.). Sodium hydrogen carbonate (2 g.) was added and oxygen was passed through the mixture with stirring at 60° C. until thin layer chromatography indicated that reaction was complete. The mixture was filtered through diatomaceous earth. The filtrate was acidified to pH5 using 2M hydrochloric acid and then extracted with ethyl acetate (4×100 ml.). The combined extracts were washed with saturated brine (150 ml.), dried ($MgSO_4$) and evaporated. The residual oil was purified by flash column chromatography, eluting with toluene-/ethyl acetate/acetic acid (70: 30: 2 v/v) to give 3-(m-[2,2-dimethyl-4-phenyl-1,3-cis 5-ylmethyl]phenyl)-propanoic acid as a colourless oil which rapidly crystallised to give solid (390 mg.), m.p. 106°–109° C.; NMR : 1.5 (3H,s), 1.55 (3H,s), 1.6–3.1 (7H,m), 3.4–4.2 (2H,m), 5.2 (1H,d, J=3Hz), 6.7–7.6 (9H,m) and 8.2–8.9 (1H,br s)ppm.

The starting material was obtained as follows:

(a) Sodium borohydride (6 g.) was added in portions to a stirred solution of m-formylcinnamic acid (22 g.), in a mixture of ethanol (300 ml.) and ethyl acetate (300 ml.) and stirring was continued for 4 hours. The mixture was cooled with ice/water, acidified with 2M hydrochloric acid (200 ml.) and extracted with ethyl acetate (4×100 ml.). The combined extracts were washed with saturated brine (150 ml.), dried ($MgSO_4$) and evaporated to give m-hydroxymethylcinnamic acid (P) as a white solid (22 g.); NMR: 4.6 (2H,s), 6.4 (1H,d,J=15Hz), and 7.2–7.7 (5H,m)ppm. This solid was used without purification.

(b) A mixture of P (22 g.) in concentrated sulphuric acid (1 ml) and absolute alcohol (500 ml.) was heated under reflux for 36 hours and allowed to cool. The solvent was evaporated and the residue was diluted with water (200 ml.). The mixture was extracted with ether (4×100 ml.). The combined extracts were washed with satured brine (200 ml.) dried ($MgSO_4$) and evaporated to give an oil. Flash column chromatography, eluting with petrol (60°–80° )/ethyl acetate (1:1 v/v) gave ethyl m-hydroxymethylcinnamate (Q) as a colourless oil (22 g.); NMR: 1.4 (3H,t), 4.3 (2H,q), 4.8 (2H,s), 6.5 (1H,d, J=15Hz) and 7.2–7.8 (5H,m)ppm. This oil was used without further purification.

(c) A solution of Q (22 g.) in absolute ethanol (500 ml.) was hydrogenated using Adams ctalyst (1 g.). The mixture was separated by filtration and the filtrate evaporated to give ethyl 3-(m-hydroxymethylphenyl)-propanoate (R) (17 g.) as an oil; NMR: 1.2 (3H,t), 2.4–3.1 (4H,m), 4.1 (2H,q), 4.6 (2H,s) and 7.0–7.4 (4H,m)ppm. This oil was used without further purification.

(d) To a stirred solution containing R (14 g.) and carbon tetrabromide (44 g.) in dry DMF (140 ml.) was added a solution of triphenylphosphine (34.5 g.) in dry DMF (130 ml.) at such a rate that the temperature did not exceed 10° C. After the addition was complete, stirring was contained for 2 hours. The mixture was then poured into ice water (1 l.). The mixture was extracted with ethyl acetate (4×150 ml.). The combined extracts were dried ($MgSO_4$) and evaporated to give an oil which after flash column chromatography, eluting with petrol (60°–80° )/ethyl acetate (85:15 v/v), gave ethyl 3-(m-bromomethylphenyl)propanoate (S) as a colourless oil (14.1 g.) which was used immediately in the next step.

(e) Using an analogous procedure to that described in part (i) of Example 1, there was obtained ethyl 2-benzoyl-3 (m-[2 (ethoxycarbonyl)ethyl]phenyl) propanoate (T) as a colourless oil; NMR: 1.2 (6H,m), 2.4–3.1 (4H,m), 3.3 (2H,d), 4.1 (4H,m), 4.6 (1H,t) and 6.8–8.1 (9H,m)ppm.

(f) Using an analogous procedure to that described in part (ii) of Example 1, there was obtained the erythro isomer of ethyl 3 (m-[2-ethoxycarbonyl)ethyl]phenyl)2-dihydroxybenzyl-propanoate (U) as a colourless oil; NMR: 0.9 (3H,t), 1.2 (3H,t), 2.4–3.1 (6H,m), 3.85 (2H,q), 4.1 (2H,q), 5.0 (1H,br s) and 6.8–7.5 (9H,m)ppm.

(g) Using an analogous procedure to that described in part (iii) of Example 1, there was obtained erythro 3-[m-(3-hydroxypropyl)phenyl]-2-α-hydroxybenzyl-propanol (V) as a colourless oil, which solidified on standing; NMR: 1.6–2.0 (2H,m), 2.5–2 5.05 (1H,d J–3.6 Hz) and 6.8–7.5 (9H,m)ppm. [Note: both ester groups are reduced by this procedure.]

(h) Using an analogous procedure to that described in part (iv) of Example 1, there was obtained (4,5-cis)5-[m-(5, 5-dimethyl 4,6-dioxaheptyl)benzyl]-2,2- dimethyl-4-phenyl-1,3-dioxane (W) as a colourless oil; NMR: 1.3 (6H,s), 1.53 (3H,s), 1.58 (3H,s), 1.7–3.5 (9H,m), 3.2 (3H,s), 3.5–4.2 (2H,m), 5.3 (1H,d J=3Hz) and 6.7–7.5 (9H,m)ppm.

(i) Using an analogous procedure to that described in part (g) of Example 2, there was obtained 3-(m-[2,2-dimethyl-4-phenyl-1,3-dioxan-cis-5ylmethyl]phenyl)-propanol (X) as a colourless oil; NMR: 1.5 (6H,br s), 1.6–3.0 (7H,m), 3.4–4.2 (4H,m), 5.2 (1H,d, J=2.6 Hz) and 6.7–7.4 (9H,m)ppm.

EXAMPLE 6

An illustration of a pharmaeutical composition suitable for administration to man for therapeutic purposes is a capsule containing a compound of formula I (such as that described in Example 3) or a salt as appropriate (2–300 mg.) together with powdered lactose (596.5–298.5 mg.) and magnesium stearate (1.5 mg.) i.e. 600 mg. of dry ingredients).

Formulae

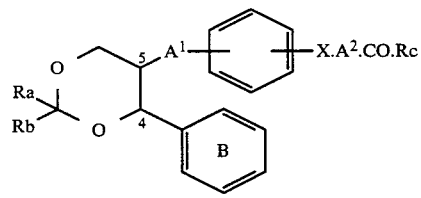

I

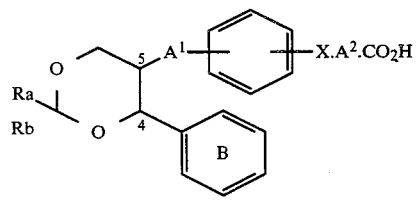

Ia

-continued
Formulae
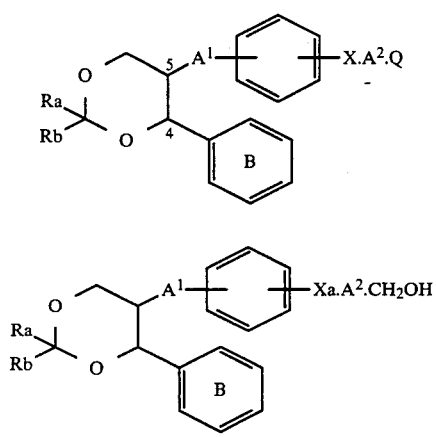
II
III
-continued
Formulae
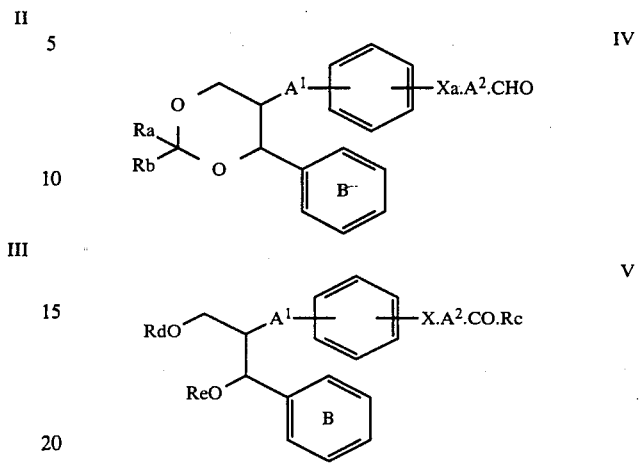
IV
V
Scheme 1
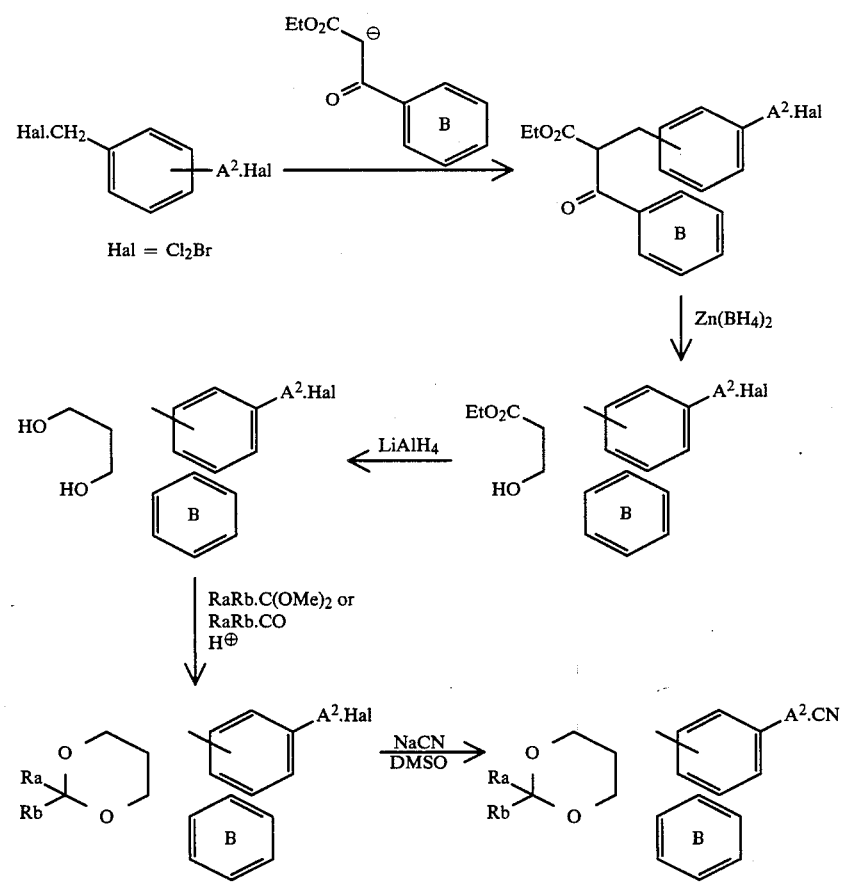
II ($A^1$ = $CH_2$, Q = CN)
X = direct bond Scheme 2

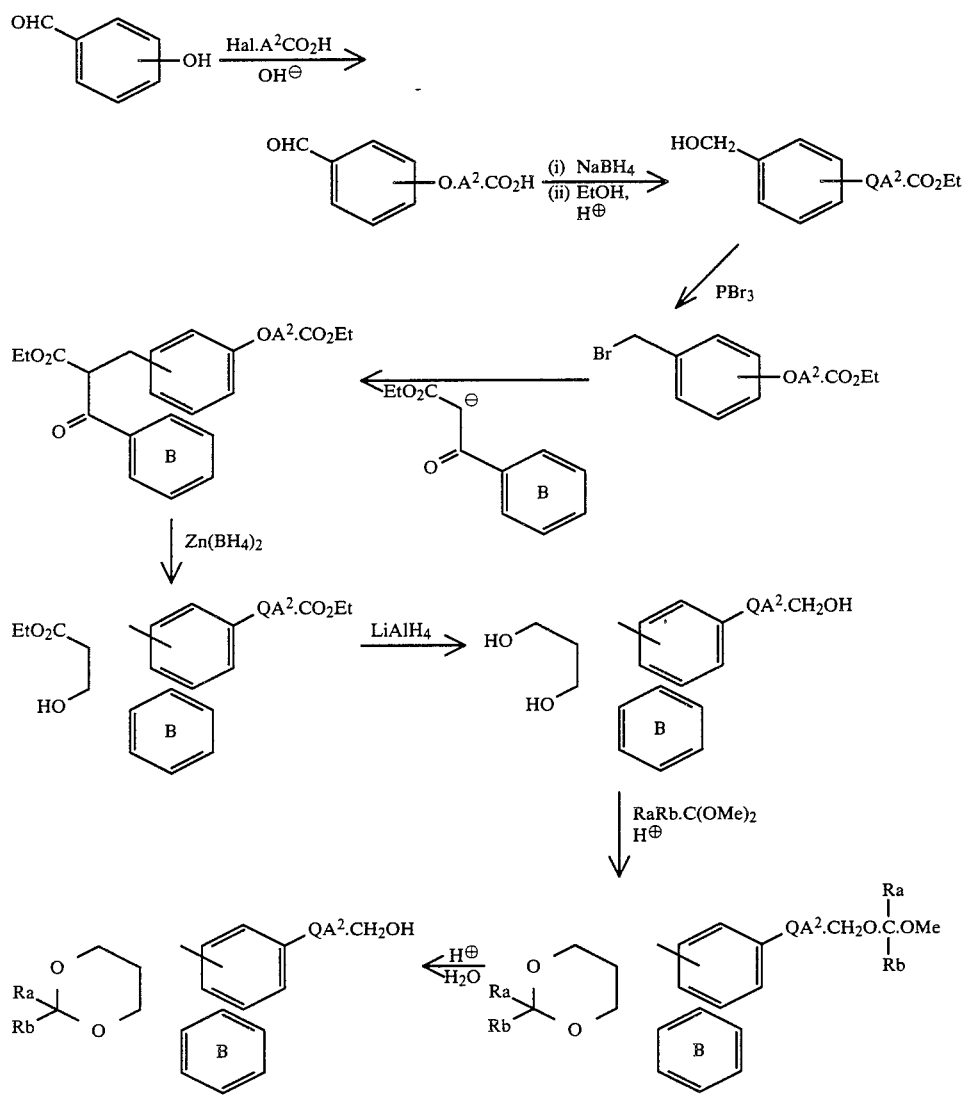

III (X = O, A² = CH₂)

What is claimed is:

1. A [(4-phenyl-1,3-dioxan-cis-5-yl)alkyl]-phenylalkanoic acid derivative of the formula I

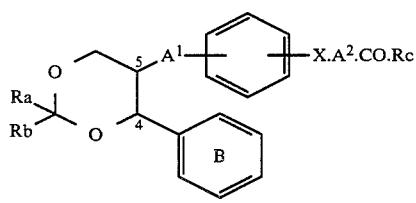

set out herein, wherein Ra and Rb are independently hydrogen, (2-6C)alkenyl, (1-8C)alkyl optionally bearing up to three halogeno substituents, or phenyl or benzyl optionally bearing up to three nuclear substituents selected from halogeno, (1-6C)alkyl, (1-6C)alkoxy, (1-4C)alkylenedioxy, trifluoromethyl, cyano, nitro, hydroxy, (2-6C)alkanoyloxy and (1-6C)alkanoylamino, provided that when Ra and Rb are both other than hydrogen the total number of carbon atoms in Ra and Rb taken together is 8 or less; or Ra and Rb together form (2-7C)polymethylene optionally bearing (1-4C)alkyl; Rc is hydroxy, (1-6C)alkoxy or (1-6C)alkanesulphonamido; A¹ and A² are independently (1-4C)polymethylene optionally bearing a methyl substituent such that the total number of carbon atoms in A¹ and A² taken together is 5 or less; X is oxygen, sulphur or a direct bond; and benzene ring B optionally bears one or two substituents selected from halogeno, (1-6C)alkyl, (1-6C)alkoxy, hydroxy, (2-6C)alkanoyloxy, (1-6C)alkanoylamino, trifluoromethyl and nitro; and the substituents at positions 4 and 5 of the dioxane ring have cis-relative stereochemistry; or for those compounds wherein Rc is hydroxy, a salt thereof with a base affording a physiologically acceptable cation.

2. A compound as claimed in claim 1 wherein Ra and Rb are independently selected from hydrogen, methyl, ethyl, propyl, isopropyl, butyl, pentyl, hexyl, heptyl and octyl, each optionally bearing up to three fluorine or chlorine atoms, and from vinyl, allyl, 2-methylallyl, phenyl and benzyl, the latter two themselves optionally bearing up to three nuclear substituents selected from fluoro, chloro, bromo, iodo, methyl, ethyl, propyl, isopropyl, methoxy, ethoxy, propoxy, methylenedioxy, ethylenedioxy, trifluoromethyl, cyano, nitro, hydroxy, acetoxy, propionyloxy, formamido, acetamido and propionamido, provided that when Ra and Rb are both other than hydrogen the total number of carbon atoms in Ra and Rb taken together is 8 or less; or Ra and Rb together form ethylene, trimethylene, tetramethylene, pentamethylene or hexamethylene, optionally bearing a methyl substituent; Rc is hydroxy, methoxy, ethoxy, methanesulphonamido, ethanesulphonamido, propanesulphonamido or 1-methylethanesulphonamido; $A^1$ and $A^2$ are independently selected from methylene, ethylene, trimethylene and tetramethylene, optionally bearing a methyl substituent, such that the total number of carbon atoms in $A^1$ and $A^2$ taken together is 5 or less; and benzene ring B optionally bears one or two substituents selected from fluoro, chloro, bromo, iodo, methyl, ethyl, propyl, isopropyl, methoxy, ethoxy, propoxy, hydroxy, acetoxy, propionyloxy, formamido, acetamido, propionamido, trifluoromethyl and nitro.

3. A compound as claimed in claim 1 wherein Ra and Rb are independently selected from hydrogen, methyl, ethyl, propyl, isopropyl, butyl, pentyl, hexyl, octyl, vinyl, allyl, 2-methylallyl, trifluoromethyl, chloromethyl, 2-chloroethyl, phenyl optionally bearing a fluoro, chloro, bromo, methyl, methoxy, trifluoromethyl, nitro, hydroxy, cyano, acetamido or methylenedioxy ituent, dichlorophenyl, dimethylphenyl, and benzyl; or Ra and Rb together form trimethylene, pentamethylene or hexamethylene, optionally bearing a methyl substituent; and benzene ring B is selected from phenyl, 2-methylphenyl, 2-ethylphenyl, 2-isopropylphenyl, 2-methoxyphenyl, 2-fluorophenyl, 2-chlorophenyl, 2-bromophenyl, 2-hydroxyphenyl, 2-trifluoromethylphenyl, 3-trifluoromethylphenyl, 3-fluorophenyl, 3-chlorophenyl, 4-fluorophenyl, 4-methylphenyl and 2,6-difluorophenyl.

4. A compound of the formula Ia

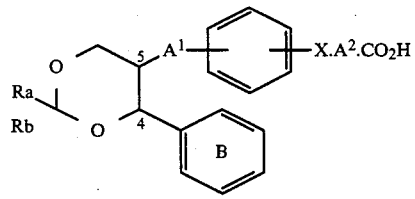

wherein:

(i) Ra and Rb are both hydrogen, methyl, ethyl, propyl, butyl or trifluoromethyl;
(ii) or together form trimethylene, tetramethylene, pentamethylene, hexamethylene or a group of the formula:, —CH$_2$CH$_2$ CHCH$_3$ CH$_2$CH$_2$—; or
(iii) Ra is (3–8C)alkyl, trifluoromethyl, chloromethyl, 2-chloroethyl, benzyl or phenyl, the last of which may optionally bear 1 or 2 halogeno, (1–4C)alkyl, (1–4C)alkoxy, trifluoromethyl, hydroxy, cyano or (1–4C)alkanoylamino substituents, or a methylenedioxy substituent, and Rb is hydrogen;

benzene ring B is unsubstituted or is 2-halogeno-, 2-(1–4C)alkyl-, 2-(1–4C)alkoxy-, 2-hydroxyor 3-halogeno-phenyl; $A^1$ and $A^2$ have the meanings defined in claim 2; $X^1$ is oxygen or a direct bond; and Ra and the substituents at the 4 and 5-positions of the dioxane ring have cis-relative stereochemistry; or a salt thereof with a base affording a physiologically acceptable cation; or a methyl or ethyl ester thereof; or a methanesulphonamido, ethanesulphonamido or 1-methylethanesulphonamido derivative thereof.

5. A compound as claimed in claim 4 wherein Ra is isopropyl, butyl, hexyl, octyl, trifluoromethyl, chloromethyl, 2-chloroethyl, benzyl or phenyl, the last two of which may optionally bear 1 or 2 substituents selected from fluoro, chloro, bromo, methyl, methoxy, trifluoromethyl, hydroxy, cyano and acetamido, or a methylenedioxy substituent, and Rb is hydrogen.

6. A compound as claimed in claim 4 wherein $A^1$ is methylene; the group X.$A^2$ is ethylene, oxymethylene or trimethylene; and benzene ring B is selected from unsubstituted phenyl, 2-fluoro-, 2-chloro-, 3-fluoro-, 3-chloro-, 2-methyl-, 2-ethyl-, 2-isopropyl-, 2-methoxy- and 2-hydroxy-phenyl.

7. The compound 4-(o-[2,2-dimethyl-4-o-hydroxyphenyl-1,3-dioxan-cis-5-ylmethyl]phenyl)butanoic acid, or a salt thereof with a base affording a physiologically acceptable cation.

8. A salt as claimed in claim 1 or 4 which is selected drom an alkaline earth metal, aluminium and 20ammonium salt and from those/salts with organic amines or quaternary bases, which form a physiologically acceptable cation.

9. A pharmaceutical composition for use in antagonising one or more of the actions of thromboxane $A_2$ comprising an antagonistically effective amount of a compound of formula I, or a salt thereof, with a base affording a physiologically acceptable cation, as claimed in claim 1 together with a pharmaceutically acceptable carrier or diluent.

10. A method for antagonising one or more of the actions of thromboxane $A_2$ in a warm-blooded animal requiring such treatment which comprises administering to said animal a thromboxane $A_2$ antagonistically effective amount of a compound of formula I as defined in claim 1 or, when Rc is hydroxy, a salt of said compound with a base affording a physiologically acceptable cation.

* * * * *